Figure 3A:
Figure 3B:
Figure 3C:
Figure 3D:

United States Patent [19]

Del Conte

[11] 4,200,091

[45] Apr. 29, 1980

[54] CONTRACEPTIVE INTRAUTERINE DEVICE

[76] Inventor: Maria L. Del Conte, Scala Campi Elisi, 1, Trieste, Italy

[21] Appl. No.: 896,702

[22] Filed: Apr. 17, 1978

[30] Foreign Application Priority Data

Nov. 23, 1977 [ES] Spain .................................. 232.273

[51] Int. Cl.² ............................................. A61F 5/46
[52] U.S. Cl. .................................................. 128/130
[58] Field of Search ....................... 128/130, 127, 260

[56] References Cited

U.S. PATENT DOCUMENTS

| | | | |
|---|---|---|---|
| 3,306,286 | 2/1967 | Ahmed | 128/130 |
| 3,457,915 | 7/1969 | Eshelman | 128/130 |
| 3,516,403 | 6/1970 | Cournut | 128/130 |
| 3,786,808 | 1/1974 | Lerner | 128/130 |
| 3,842,826 | 10/1974 | Nolan | 128/130 |
| 3,889,666 | 6/1975 | Lerner | 128/127 |

*Primary Examiner*—Lawrence W. Trapp
*Attorney, Agent, or Firm*—Joseph W. Molasky & Associates

[57] ABSTRACT

A woman's contraceptive in the form of an intrauterine device, having an elastic structure in the form of a stylized inverted Delta which, when viewed in profile, possesses a rectangular shape over its entire cross-section, and which comprises an arc internal to the Delta-shaped structure at the center of which there is a channel through which a monofilament is knotted, to descend double and pass through a hole provided in the center of the lower arc of the Delta, said device being adaptable to the variable shape of the uterine cavity so as to avoid causing injury.

3 Claims, 6 Drawing Figures

CONTRACEPTIVE INTRAUTERINE DEVICE

This invention relates to a new intrauterine device for use as a woman's contraceptive. This device is totally different from known devices and is characterised by a completely individual form.

BACKGROUND

Fertility control methods must be effective and safe and should afford no more than a minimum of side-effects both in terms of frequency and intensity.

Based on present knowledge a contraceptive must satisfy the following requirements in order to afford the maximum guarantees from a medical and psychological-social standpoint:

(1) Pearl and mathematical index as close as possible to 0.
(2) Minimum production of side-effects and with the smallest possible frequency.
(3) Minimum damage to the gyneco-endocrinal system.
(4) Minimum medical contraindications.
(5) Low medical extraction index.
(6) Very low expulsion index.
(7) Very high index of continuity or permanency.
(8) Contraceptive effect which lasts for years.
(9) Ability to be fitted easily not only by medical personnel, but also by paramedical personnel in case of need, with minimum risk to the patient.
(10) No need for continual medical inspection.
(11) Return of fertily on removing the contraceptive.

THE INVENTION

The device of this invention has the overall form of an inverted stylised letter Delta. Seen in profile, it has a rectangular cross-section.

More specifically, this device relates to an elastomeric intrauterine contraceptive in the form of a stylised inverted Delta which, in profile, possesses a rectangular shape over its entire cross-section, and which comprises an arc internal to the Delta-shaped structure at the center of which there is a channel through which a monofilament is knotted to descend double and pass through a hole provided in the center of the lower arc of the Delta, said device being adaptable to the variable shape of the uterine cavity.

The present device will now be described by reference to the accompanying Drawings showing one particular embodiment by way of example.

Figure 1:
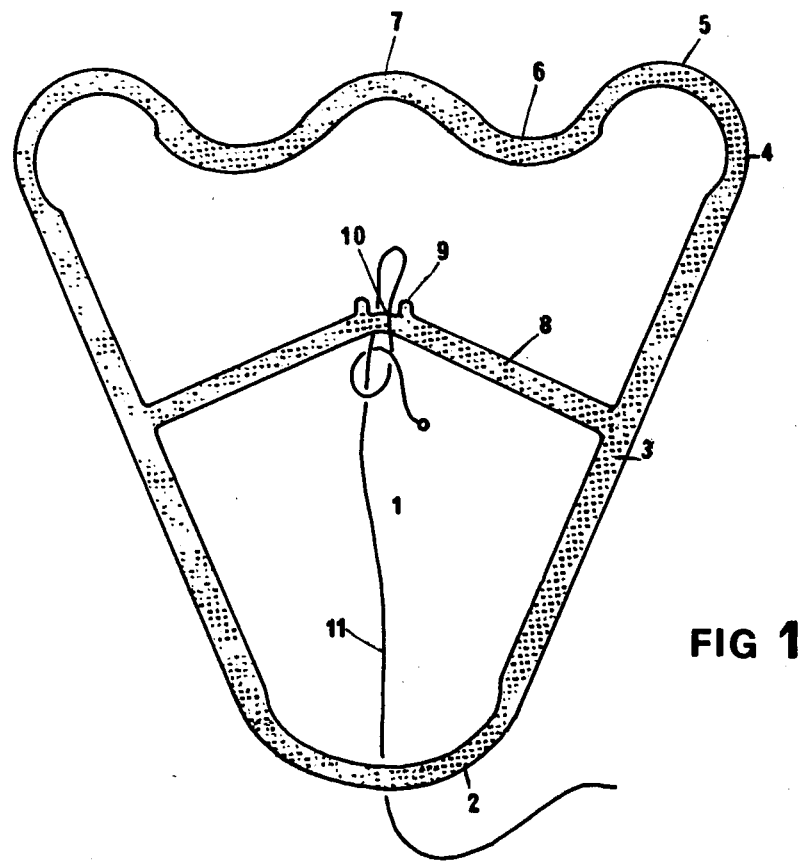
Figure 2:
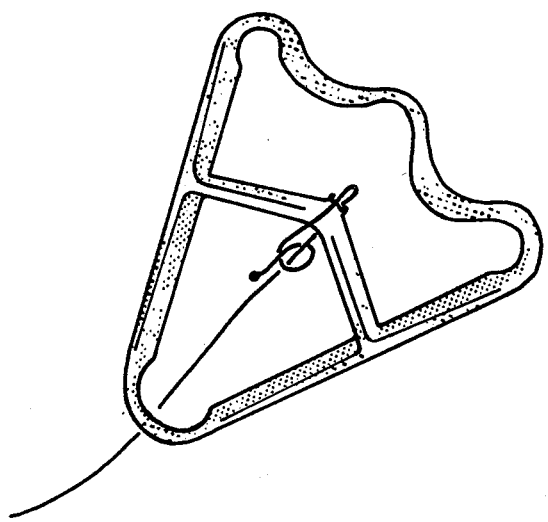

FIG. 1 is a side view of the device of this invention.
FIG. 2 is a perspective view of the device of FIG. 1.
FIGS. 3a-3d illustrate several shapes which the device of FIG. 1 assumes during use.

In FIG. 1, beginning with the lower base of the device 1 at its longitudinal axis and proceeding along the right hand side there is a small arc 2 of a circle followed by a straight ascending line 3 inclined at about 45° to said base. This straight line occupies nearly the entire length of the device and constitutes it main member. At the top part connected to the side 3, the device comprises a slight contraction 4 and then continues in the form of a half circle 5 disposed in the opposite direction to the base arc and terminating a little higher than the plane passing through its initial point. The circle arc 6 which follows is inverted relative to the previous arc and remains lower than the latter. Said arc 6 is connected to another arc 7 disposed in the same direction as arc 5 and terminating at the longitudinal axis of the device. This entire upper part of the device, beginning at the contracting point at the main member has the overall shape of an undulating line. A straight portion 8 branches off at about three quarters the height of the main member in an ascending direction towards the longitudinal axis, and before intersecting said longitudinal axis there appears a protuberance 9 which occupies the entire cross-section of said portion 8.

The left hand side of the device has the same shape as the right hand side described above in that the device is symmetrical and has been divided along an imaginary longitudinal axis only for ease of description.

A descending thread 11 branches from the central part of the device, that is, from the transverse channel 10 formed by the two proturberances 9, and said thread is passed through a hole formed in the center of the lower base 2 of the device.

The preferred dimensions of this new device, in frontal view, before being fitted, are as follows:

| | |
|---|---|
| maximum horizontal width: | 29.5 mm |
| maximum vertical width: | 31.0 mm |
| thickness: | 3.0 mm |

The device of this invention has the following technical and scientific advantages:

(1) It is suitably designed for the matrix and takes account of its anatomophysiology.
(2) It is designed for the woman who has given birth once or more times.
(3) Its measurements, elasticity and flexibility mean that a single model is sufficient for the woman who has given birth more than once.
(4) It has no points which could produce injury.
(5) It is smooth and slidable.
(6) It adapts to the shape of the uterine cavity (perimeter).
(7) It moves with uterine contractions and adapts to changes in the cavity.
(8) Its elastic flexibility strength has been calculated such that it is less than the force of contraction of the myometrium, because of which it cannot harm it and cannot pass into the abdominal cavity.
(9) It provides a minimum possibility of expulsion even for the woman who has given birth more than once and comprises a dehiscent neck with injury.

The device of this invention is inert, being constructed of biologically non-degradable material which cannot cause pathological reactions with tissue. It does not give rise to harmful chemical reactions and contains no metals or hormones which could cause allergic reactions, toxicity or metaplastic alterations to the hormone-dependent tissues.

Because of its design, the present device is the only one which need not be inserted as far as the uterine base and it is the only one which becomes released in the uterine cavity, on the inner face of the internal orifice of the neck of the uterus.

This fact leads to the exceptional advantage of preventing any danger of perforating the matrix when locating it. All other known devices run this risk.

The applicator for the new device is inserted only into the semi-straight section of the neck, while only the device itself passes the uterine flexo-versions, and once it has passed the internal orifice of the neck it opens and slides smoothly as far as the uterine base, adapting to the uterine cavity independently of whether there exits any front, rear or lateral versions or flexion of the matrix.

In the large majority of cases, neither the Pozzi forceps nor the hysterometer are necessary.

With a minimum of practice it can be fitted by general practitioners without any danger of perforation. This danger has limited the use of other devices as contraceptives, even though this is the most economical method, and a method which functions independently of the patient.

The intrauterine device of the present invention is elastic and, therefore, it can follow the movements of the uterus and adapt to changes in the cavity without causing injury. Its diameters vary and reduce with uterine contraction. This is evident from FIG. 3.

What is claimed is:

1. An intrauterine contraceptive device which is symmetrical on both sides of its longitudinal axis and comprising on one side of said axis:
   (1) a base consisting of a small base arc which connects to a straight ascending line inclined at an angle to said base and wherein said line is connected at its topmost extremity to a top portion which is in the form of a half circle disposed in a direction opposite to that of said base arc;
   (2) said half circle continuing in the form of an inverted arc which is connected to still another arc to afford the overall shape of an undulating line which terminates at the upper longitudinal axis of said device; and
   (3) the straight ascending line also includes a straight branch portion which branches off in an ascending direction toward the longitudinal axis and which, before intersecting said axis, provides a protuberance which occupies the entire cross-section of said portion; including
   (4) a descending thread connected to the straight branch portion at about the central part of said device between its protuberances, said thread being passed through a hole in the center of said lower base of said device.

2. The device of claim 1 wherein the straight ascending line is inclined at an angle of about 45° to said small base arc.

3. The device of claim 1 wherein the straight branch portion branches off at about three quarters the height of said straight ascending line.

* * * * *